(12) United States Patent
Fleurot et al.

(10) Patent No.: US 6,255,264 B1
(45) Date of Patent: Jul. 3, 2001

(54) DETERGENT COMPOSITION CONTAINING A BENEFIT AGENT MADE UP OF AGGREGATED PARTICLES

(75) Inventors: Olivier Fleurot; Robert Stanley Lee, both of Wirral (GB)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/459,486

(22) Filed: Dec. 13, 1999

(30) Foreign Application Priority Data

Dec. 15, 1998 (GB) .................................. 9827614

(51) Int. Cl.$^7$ ................................. C11D 3/37; C11D 1/37
(52) U.S. Cl. .................. 510/124; 510/119; 510/121; 510/122; 510/123; 510/127; 510/130; 510/135; 510/151; 510/152; 510/153; 510/155; 510/156; 510/242; 510/417; 510/434; 510/437; 510/466; 510/490
(58) Field of Search ...................... 510/119, 121, 510/122, 123, 127, 130, 135, 151, 152, 153, 155, 156, 242, 417, 434, 437, 466, 490

(56) References Cited

U.S. PATENT DOCUMENTS

| | | | | |
|---|---|---|---|---|
| 4,364,837 | * | 12/1982 | Pader | 252/173 |
| 5,085,857 | * | 2/1992 | Reid et al. | 424/70 |
| 5,152,914 | * | 10/1992 | Forster et al. | 252/174 |
| 5,246,694 | * | 9/1993 | Birtwistle | 424/70 |
| 5,409,628 | * | 4/1995 | Heinz et al. | 252/174.17 |
| 5,441,730 | * | 8/1995 | Gough et al. | 424/70.11 |
| 5,500,152 | * | 3/1996 | Helliwell | 252/547 |
| 5,720,964 | * | 2/1998 | Murray | 424/401 |
| 5,747,435 | * | 5/1998 | Patel | 510/119 |
| 5,747,436 | * | 5/1998 | Patel et al. | 510/124 |
| 5,833,999 | * | 11/1998 | Trinh et al. | 424/401 |
| 5,977,038 | * | 11/1999 | Birtwistle et al. | 510/122 |
| 6,022,836 | * | 2/2000 | Dubief et al. | 510/122 |
| 6,026,534 | * | 2/2000 | Gonda et al. | 15/207.2 |

FOREIGN PATENT DOCUMENTS

| | | |
|---|---|---|
| 0136914 | 4/1985 | (EP) . |
| 90/13283 | 11/1990 | (WO) . |
| 94/01084 | 1/1994 | (WO) . |
| 95/22311 | 8/1995 | (WO) . |
| 96/17592 | 6/1996 | (WO) . |
| 97/45525 | 12/1997 | (WO) . |

* cited by examiner

*Primary Examiner*—Yogendra Gupta
*Assistant Examiner*—Charles Boyer
(74) *Attorney, Agent, or Firm*—Ronald A. Koatz

(57) ABSTRACT

An aqueous liquid cleansing and moisturising composition comprising:

a) a surface active agent selected from anionic, nonionic, zwitterionic and cationic surface active agents, soap and mixtures thereof;

b) a benefit agent; and c) a cationic polymer characterised in that the cationic polymer is present in the composition at levels of 0.05–3.0% by weight, and that the benefit agent is present in the neat composition as aggregated particles.

18 Claims, No Drawings

DETERGENT COMPOSITION CONTAINING A BENEFIT AGENT MADE UP OF AGGREGATED PARTICLES

The present invention relates to detergent compositions suitable for topical application for cleansing and improving the condition of the human body, particularly for moisturising the skin, hair, nails and other epithelial tissues, including the mucosae. In particular, it relates to compositions which are formulated to give mild cleansing and conditioning of the skin, and improved deposition of benefit agents.

Compositions formulated to cleanse the skin are well known. It is also known to formulate products which provide both a cleansing and a moisturising benefit.

For example WO 90/13283 discloses a composition comprising an acyl ester of an isethionic acid salt, a long chain fatty acid, a moisturiser component and, optionally, soap.

One of the problems which may be encountered with such dual purpose compositions is that they contain either an insufficient level of moisturiser component, or that an insufficient amount is deposited on use. In particular in the context of the second problem, insufficient deposition means that a large proportion of the benefit agent which is in the composition is wasted.

We have found a way of formulating such compositions such that they can deliver effective moisturising, conditioning and/or protection of the skin, and also a way of delivering benefit agents in a more efficient manner.

Thus, according to a first aspect of the invention, there is provided an aqueous liquid cleansing and moisturising composition comprising:
 a) a surface active agent selected from anionic, nonionic, zwitterionic and cationic, surface active agents, soap and mixtures thereof;
 b) a benefit agent; and
 c) a cationic polymer characterised in that the cationic polymer is present at levels of 0.05–3% by weight, and that the benefit agent is present in the neat composition as aggregated particles.

Compositions according to the invention are preferably shear thinning.

An advantage of compositions according to the present invention is that they lead to improved deposition of benefit agents from a surfactant containing aqueous liquid composition during use.

We have surprisingly found in compositions according to the invention that particles of the skin benefit agent form aggregates which comprise a number of individual particles. Aggregates which characterise compositions according to the invention may typically comprise 5–5000 individual particles of benefit agent. Without wishing to be bound by theory, it is suspected that compositions which comprise these aggregated particles, which aggregated particles stay in this form and do not coalesce, serve to deliver to the substrate relatively large aggregates of benefit agent, which provides an effective local high concentration of the benefit agent, thus enhancing the moisturising benefit to the substrate, and also the overall efficiency of delivery of the benefit agent.

As such, compositions according to the invention may typically comprise relatively high populations of relatively large, aggregated particles. Compositions according to the invention may therefore for example have a mean individual particle size of less than 5 microns, typically less than 1 micron, but contain about 50% or less by weight of the benefit agent in the composition in particles less 3 microns in size. Typically the composition may also comprise less than 10% by weight of the benefit agent in aggregated particles of greater than 80 microns in size. Compositions according to the invention typically have more than 3% by weight of the benefit agent in aggregated particles with sizes in the range 3–80 microns.

Compositions according to the invention also characteristically retain the aggregated microstructure during dilution in use, for example when diluted by a factor of 10 with distilled water. As such, compositions which have been diluted at ratios between 1:1 and 1:100 with water have been found also to retain the microstructure.

Compositions according to the invention, in particular containing the aggregated particles described, preferably contain not only relatively high levels of benefit agent, cationic polymer, and contain aggregated particles of benefit agent, but may conveniently also be made according to preferred process aspects. In the preferred process, it is important that the relatively high level of cationic polymer is sufficiently dispersed in the aqueous vehicle of the invention such that the product will have a smooth (i.e. not textured or lumpy) appearance. This can be quite difficult with the relatively high levels of cationic polymer in the composition, but is nevertheless within the remit of the skilled person to achieve.

The following also represent preferred aspects of the process of manufacture of compositions according to the invention:

a) The skin benefit agent should be prepared as a pre-emulsion, which is heated to 50–70° C.

b) The surfactant components of the composition are prepared as a solution, and the skin benefit agent pre-emulsions from a) are blended into the surfactant solution.

c) The cationic polymers are pre-dispersed in water in a controlled manner such that the rate of hydration of the cationic polymer is controlled if necessary. This can for example be done by dispersing the dried cationic polymer in a solution of pH at least 10, preferably greater than 11, to control hydration of the polymer, before dispersing it in the other components of the composition. Incomplete distribution of the cationic polymer is typified by a grainy appearance of the composition, or the presence of globules of undissolved polymer. Alternatively, the cationic polymer can be dispersed in a non-aqueous liquid component of the composition, such as eg glycerol. However, in such a situation the non-aqueous component must be present in the composition at sufficient and suitable levels so as to provide satisfactory, non-lumpy dispersion of the cationic polymer which will disperse satisfactorily in the aqueous vehicle. In any event, it is highly preferable that the cationic polymer is fully dispersed in the aqueous vehicle prior to it being fully hydrated.

d) Following the sequence of steps a)–c) above, the remaining components of the composition, with the exception of the perfume and preservatives, are blended together and maintained at or around 50–70° C. Complete mixing is preferably attained by subjecting the composition to high shear at this stage, but in such a manner that aeration of the composition is avoided; the high shear stage can typically take 20 minutes.

e) Following the sequence of steps a)–d), the composition is cooled to 30° C. where the minors (eg perfume, preservative) are added, and the viscosity is modified by the addition of the appropriate viscosity modifying agent.

In any event, it is preferred that the cationic polymer used in compositions according to the invention is at least partially hydrated when it is dispersed in the aqueous vehicle. If the cationic polymer is insufficiently hydrated, this may lead to insufficient aggregation of the droplets of benefit agent in the composition, whilst if the cationic polymer is overly hydrated, in particular during its dispersion in the composition, it may prove difficult to disperse satisfactorily.

The composition according to the invention is suitable for cleansing and "moisturising", "conditioning" or "protection" of the skin. The benefit agent is included in the composition to moisturise, condition and/or protect the skin. By "benefit agent" is meant a substance that softens the skin (stratum corneum) and keeps it soft by retarding the decrease of its water content and/or protects the skin.

Preferred benefit agents, which may be solid or liquid at room temperature, but for the sake of simplicity of terminology herein are referred to as "particles", include:

a) silicone oils, gums and modifications thereof such as linear and cyclic polydimethylsiloxanes, amino, alkyl alkylaryl and aryl silicone oils;
b) fats and oils including natural fats and oils such as jojoba, soyabean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;
c) waxes such as carnauba, spermaceti, beeswax, lanolin and derivatives thereof;
d) hydrophobic plant extracts;
e) hydrocarbons such as liquid paraffins, petroleum jelly, microcrystalline wax, ceresin, squalene, squalane, and mineral oil;
f) higher fatty acids such as lauric, myristic, palmitic, stearic, behenic, oleic, linoleic linolenic, lanolic, isostearic and poly unsaturated fatty acids (PUFA) acids;
g) higher alcohols such as lauryl, cetyl, steryl, oleyl, behenyl, cholesterol and 2-hexadecanol alcohol;
h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;
i) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;
j) lipids such as cholesterol, ceramides, sucrose esters and pseudo-ceramides as described in European Patent Specification No. 556 957;
k) vitamins such as vitamin A and E, and vitamin alkyl esters, including those vitamin C alkyl esters;
l) sunscreens such as octyl methoxyl cinnamate (Parsol MCX) and butyl methoxy benzoylmethane (Parsol 1789)
m) phospholipids; and
n) mixtures of any of the foregoing components.

Where adverse interactions between the benefit agent and the surfactant are likely to be particularly acute, the benefit agent may be incorporated in the compositions of the invention in a carrier. In such situations the carrier could itself be a benefit agent, such as an oil.

Such benefit agents include lipids; alkyl lactates; sunscreens; esters such as isopropyl palmitate and isopropyl myristate; and vitamins. The carrier can, for example, be a silicone or hydrocarbon oil which is not solubilised/micellised by the surface active phase and in which the benefit agent is relatively soluble.

Particularly preferred benefit agents include silicone oils, gums and modification thereof; esters such as isopropyl palmitate and myristate, and alkyl lactates.

The benefit agent is preferably present in an amount of from 1.0 to 50 wt %, most preferably from 4 to 25 wt % of the composition, more preferably 5–15%, even more preferably 5–10% by weight of the composition.

An advantage of the composition according to the invention is that, during use, it deposits benefit agent onto the skin at a level which results in a perceivable benefit.

The surface active agent can be selected from any known surfactant suitable for topical application to the human body. Mild surfactants, i.e. surfactants which do not damage the stratum corneum, the outer layer of skin, are particularly preferred. Because of their lathering properties, anionic surfactants are highly preferred components of compositions according to the invention. Where the composition contains an anionic surfactant, it is preferable that the composition also contains a co-surfactant, which can be a nonionic, cationic or zwitterionic surfactant.

One preferred anionic detergent is fatty acyl isethionate of formula:

$$RCO_2CH_2CH_2SO_3M$$

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

$$RO(CH_2CH_2O)_nSO_3M$$

where R is an alkyl group of 8 to 22 carbon atoms, n ranges from 0.5 to 10 especially from 1.5 to 8, and M is a solubilising cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula: $R^5O_2CCH_2CH(SO_3M)CO_2M$; and amido—MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein $R^5$ ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Mixtures of any of the foregoing surface active agents may also be used.

The surface active agent is preferably present at a level of from 1 to 35 wt %, preferably 3 to 30 wt % of the composition, more preferably at least 5% by weight of the composition.

It is also preferable that the composition includes from 0.5 to 15 wt % of a cosurfactant agent with skin-mildness benefits. Suitable materials are zwitterionic detergents which have an alkyl or alkenyl group of 7 to 18 carbon atoms and comply with an overall structural formula:

$$R^1-(\overset{O}{\overset{\|}{C}}-NH-(CH_2)_m)_n-\overset{R^2}{\underset{R^3}{\overset{|}{N^+}}}-X-Y$$

where $R^1$ is alkyl or alkenyl of 7 to 18 carbon atoms $R^2$ and $R^3$ are each independently alkyl, hydroxyalkyl or carboxyalkyl of 1 to 3 carbon atoms;

m is 2 to 4;

n is 0 or 1;

X is alkylene of 1 to 3 carbon atoms optionally substituted with hydroxyl; and

Y is $-CO_2^-$ or $-SO_3^-$.

Zwitterionic detergents within the above general formula include simple betaines of formula:

$$R^1-\overset{R^2}{\underset{R^3}{\overset{|}{N^+}}}-CH_2CO_2^-$$

and amido betaines of formula:

$$R^1-CONH-(CH_2)_m-\overset{R^2}{\underset{R^3}{\overset{|}{N^+}}}-CH_2CO_2^-$$

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the group $R^1$ has 10 to 14 carbon atoms. $R^2$ and $R^3$ are preferably methyl.

A further possibility is a sulphobetaine of formula:

$$R^1-\overset{R^2}{\underset{R^3}{\overset{|}{N^+}}}-(CH_2)_3SO_3^-$$

or $$R^1-CONH(CH_2)_m-\overset{R^2}{\underset{R^3}{\overset{|}{N^+}}}-(CH_2)_3SO_3^-$$

where m is 2 or 3, or variants of these in which $-(CH_2)_3SO_3^-$ is replaced by $$-CH_2\overset{OH}{\overset{|}{C}}HCH_2SO_3^-$$

$R^1$, $R^2$ and $R^3$ in these formulae are as defined previously.

A necessary component in compositions according to the invention is a cationic polymer.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 7th edition. The ratio of the cationic to non-cationic monomer units is selected to give a polymer having a cationic charge density in the required range.

Suitable cationic polymers include, for example, copolymers of vinyl monomers having cationic amine or quarternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anyhdride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quarternization.

The cationic polymers can comprise mixtures of monomer units derived from amine- and/or quaternary ammonium-substituted monomer and/or compatible spacer monomers.

Suitable cationic polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g. GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

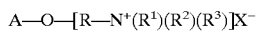

A—O—[R—N⁺(R¹)(R²)(R³)]X⁻ wherein: A is an anhydroglucose residual group, such as a starch or cellulose anhydroglucose residual, R is an alkylene, oxyalkylene, polyoxyalkylene, or hydroxyalkylene group, or combination thereof; and $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride. (Commercially available from Rhone-Poulenc in their JAGUAR trademark series).

Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hyroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar derivatives. Particularly preferred cationic polymers are JAGUAR C13S, JAGUAR C15, JAGUAR C17 and JAGUAR C16 and JAGUAR C162, especially Jaguar C13S, and cationic starches such as Softgel BDA (ex. Avebe).

Cationic polymer is present in composition at levels of 0.05–3.0%, more preferably 0.4–3.0%, even more preferably 0.5–1.5% by weight of the composition.

In preferred embodiments an auxiliary structurant may be added to the composition. Suitable materials include swelling clays, for example laponite; cross-linked polyacrylates such as Carbopol (™) (polymers available from Goodrich); acrylates and copolymers thereof; polyvinylpyrrolidone and copolymers thereof; polyethylene imines; polymeric carboxylates, consisting of and including modified and unmodified starches, unsubstituted quar gums, agars, alginates, xanthan gum, carrageenan, cellulose derivatives, exudate gum, gellan gum, gelatin, pectins and seed gums; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The composition may also comprise a viscosity modifying agent, ie a material which adjusts the viscosity of the composition to be that which is suitable for and preferred by consumers. Suitable materials include ethylene glycols, propylene glycols, salts such as sodium chloride and ammonium sulphate; and sucrose esters.

Preferred viscosity modifiers include PEG 18 glyceryl glycerol dioleococoate (Antil 171, ex. Goldschmidt), PEG 55 propylene glycol oleate (Antil 141, ex. Goldschmidt), PEG 150 distearate and PEG 150 pentaerythrityl tetrastearate (Crothix, ex Croda).

Thickeners may also be added to the benefit agent in order to achieve the required viscosity during use. Preferred thickeners for the composition include fumed silica; polyethylene; alkyl silicone waxes; aluminium silicate; lanesterol; natural and synthetic waxes; fatty acids and derivatives thereof, in particular, fatty acid monoglyceride polyglycol ethers; higher fatty alcohols; petrolatum; narogel; polyammonium stearate; hydrotalcites; and mixtures thereof. Hydrotalcites are materials of general formula

$[M_m N_n (OH)_{2(m+n)}]^{r+} X^{x-}_{n/x} y H_2 O$ where

M is a divalent metal ion e.g. $Mg^{2+}$;

N is a trivalent metal ion e.g. $Al^{3+}$;

X is an exchangeable anion e.g $CO_3^-$, $NO_3^-$; stearate, cinnimate.;

m is the number of divalent metal ions; and n is the number of trivalent metal ions.

Whilst some materials can function as both a benefit agent and a thickener therefore, it will be appreciated that the benefit and thickening function cannot be provided by the same component. However, it will be understood that where the composition comprises two or more benefit agents one of the benefit agents may also function as a thickening agent.

Further examples of structurants and thickeners are given in the International Cosmetic Ingredient Dictionary, Seventh Edition, 1997, published by CTFA (The Cosmetic, Toiletry & Fragrance Association), incorporated herein by reference.

Furthermore, the benefit agent may also function as a carrier to deliver efficacy agents to skin treated with the compositions of the invention. This route is particularly useful for delivering efficacy agents which are difficult to deposit onto the skin or those which suffer detrimental interactions with other components in the composition. In such cases the carrier is often a silicone or hydrocarbon oil which is not solubilised/micellised by the surface active phase and in which the efficacy agent is relatively soluble. Examples of such efficacy agents include anti-viral agents; hydroxycaprylic acids; pyrrolidone; carboxylic acids; 3,4,4'-trichlorocarbanilide; benzoyl peroxide; perfumes; essential oils; germicides and insect repellants such as 2,4,4'-trichloro-2'-hydroxydiphenyl ether (Irgasan DP300); salicylic acid; willow extract, N,N-dimethyl m-toluamide (DEET); and mixtures thereof.

Compositions of the invention may be formulated as products for washing the skin, for example, bath or shower gels, hand washing compositions or facial washing liquids; pre- and post-shaving products; rinse-off, wipe-off and leave-on skin care products; products for washing the hair and for dental use. Shower gels are particularly preferred product forms.

The compositions of the invention will generally be pourable liquids or semi-liquids e.g. pastes and will have a viscosity in the range 250 to 100,000 mPas measured at a shear rate of 10 s$^{-1}$ and 25° C. in a Haake Rotoviscometer RV20.

When the product is formulated as a shower gel the viscosity will generally be in the range 800 to 15000 mPas measured at a shear rate of 10 s$^{-1}$ and 25° C.

When the product is formulated as a facial wash product the viscosity will generally be in the range 3000 to 100,000 mPas measured at a shear rate of 10 s$^{-1}$ and 25° C.

Other typical components of such compositions include opacifiers, preferably 0.2 to 2.0 wt %; preservatives, preferably 0.2 to 2.0 wt % and perfumes, preferably 0.5 to 2.0 wt %.

Compositions according to the invention are also preferably deaerated or contain minimal incorporated air, in order to maximise product stability.

The invention will be further illustrated by reference to the following non-limiting examples.

EXAMPLES 1–6

The following compositions were prepared in line with the general method outlined above:

| Component | Ingredient | % of comp (wt) | | | | | |
|---|---|---|---|---|---|---|---|
| | | 1 | 2 | 3 | 4 | 5 | 6 |
| Silicone oil | 30 wt % of 50% ai emulsion (DC2-1784, ex Dow Corning), mean part.size 0.7μ | 15.0 | 15.0 | 15.0 | 15.0 | 15.0 | 15.0 |
| Betaine | 26.6 wt % of 30% ai Dehyton K (ex Henkel) | 8.0 | 8.0 | 8.0 | 8.0 | 8.0 | 8.0 |
| Sodium cocoyl isethionate | 100% ai Jordapon IC (ex PPG/Mayer) | 5.0 | 5.0 | 5.0 | 5.0 | 5.0 | 5.0 |

-continued

| Component | Ingredient | % of comp (wt) | | | | | |
|---|---|---|---|---|---|---|---|
| | | 1 | 2 | 3 | 4 | 5 | 6 |
| Sodium lauryl ether 2E0 sulphate | 7 wt % of 27% ai Genapol LRO (ex Hoechst) | 2.0 | 2.0 | 2.0 | 2.0 | 2.0 | 2.0 |
| Cationic polymer | Jaguar C13S (ex Rhone Poulenc) | 0.5 | — | — | — | — | 0.25 |
| Cationic starch | Softgel BDA (ex Avebe) | — | — | — | 0.5 | — | — |
| Polypropylene glycol 2000 | (ex Fisher) | 0.31 | 0.22 | 0.55 | 0.24 | 0.35 | 0.26 |
| Perfume | | 1.0 | 1.0 | 1.0 | 1.0 | 1.0 | 1.0 |
| BHT | | 0.5 | 0.5 | 0.5 | 0.5 | 0.5 | 0.5 |
| Formalin | 40% ai (ex Fisher) | 0.04 | 0.04 | 0.04 | 0.04 | 0.04 | 0.04 |
| Sodium polyacrylate | Carbopol 1382 (ex Goodrich) | — | — | 0.3 | — | — | — |
| Cationic polymer | Polygel K100 (ex Sigma) | — | — | — | — | 0.3 | — |
| Water | | to 100 | | | | | |

The compositions had the following viscosities (as measured with a Haake VT500):

| Example | Viscosity @ 10s$^{-1}$, 25° C. (Pa.s) |
|---|---|
| 1 | 6.4 |
| 2 | 6.5 |
| 3 | 2.5 |
| 4 | 6.1 |
| 5 | 3.2 |
| 6 | 6.2 |

The compositions according to Examples 1 to 6 were assessed for their deposition of silicone oil onto a 12 cm by 5 cm patch of porcine skin. Accordingly, porcine full thickness skin was prehydrated, and then 0.5 ml of each composition was applied to it. The skin was lathered for 30 seconds, and then rinsed with three 200 ml portions of 30° C. water. Thereafter, the skin was wiped with a paper towel to remove excess water. Two minutes after drying, a strip of adhesive tape was pressed onto the skin for 30 seconds by applying a constant load of 100 g cm$^{-2}$.

The adhesive tape employed was J-Lar Superclear™ tape having a width of 2.5 cm. Strips of tape were taken from 3 adjacent sites on the skin.

In this test procedure silicone which had deposited on the skin was subsequently transferred to the tape along with some of the outer layer of the skin.

The amounts of silicon and skin adhering to the tape were determined by means of X-ray fluorescence spectroscopy. The tape strips were placed in an X-ray fluorescence spectrometer with the adhesive side facing the beam of the machine. A mask was applied over the tape to define a standardised area in the middle of the tape which was exposed to the X-ray beam. The sample chamber of the machine was placed under vacuum before making measurements and the spectrometer was then used to measure the quantities of silicon and sulphur. The sulphur was representative of the amount of skin which has transferred to the tape.

The amounts of silicon and sulphur observed with a clean piece of adhesive tape were subtracted from the experimental measurements. The experimental measurements for the average levels of sulphur and silicon were expressed as a ratio of silicon to sulphur. From this ratio it was possible to determine silicone oil deposition per unit area of skin.

Results

| Example | Si/S ratio |
|---------|-----------|
| 1 | 10.28 |
| 2 | 1.26 |
| 3 | 4.65 |
| 4 | 11.41 |
| 5 | 11.2 |
| 6 | 8.52 |

The aggregation of silicone particles was observed and quantified using a Malvern Mastersizer. The apparatus was configured to detect silicone oil. The level employed enabled detection of silicone droplets and aggregates in the range 0.1–200 μm; the amount of shower gel composition used was selected to provide an absorbance value in the apparatus of 0.2–0.25. A small amount of shower gel was diluted under agitation in the sample presentation unit of the apparatus. Agitation was necessary to ensure that the shower gel dilution had occurred efficiently.

| Example | % Si oil with particle size in range 0.2–3.27 μ | % silicone oil with particle size in range 3.27–69.3 μm |
|---------|-----------|-----------|
| 1 | 9.38 | 60.83 |
| 2 | 97.18 | 0.26 |
| 3 | 91.19 | 2.64 |
| 4 | 50.12 | 39.33 |
| 5 | 50.24 | 45.15 |
| 6 | 34.28 | 52.38 |

The results indicate that vastly superior deposition is obtained in compositions according to the invention, where the relatively large particles comprising agglomerated individual silicone droplets have been deposited on the substrate.

What is claimed is:

1. An aqueous liquid cleansing and moisturizing composition comprising:
   a) a surface active agent selected from anionic, nonionic, zwitterionic and cationic surface active agents, soap and mixtures thereof;
   b) a benefit agent; and
   c) a cationic polymer characterized in that the cationic polymer is present in the composition at levels of 0.05–3.0% by weight, and that the benefit agent is present as aggregated particles or agglomerates which are comprised of 5–5000 individual particles; and wherein at least 3% by wt. of the composition comprises benefit agent present in the form of said agglomerates, and which agglomerates have a mean particle size of 3 microns or greater.

2. A composition according to claim 1, wherein the individual particles have mean particle sizes of less than 5 microns.

3. A composition according to claim 2, wherein the individual particles or droplets have mean particle sizes less than 1 micron.

4. A composition according to claim 1, wherein the composition comprises at least 3% by weight of the benefit agent in agglomerates of mean particle sizes 3–80 microns.

5. A composition according to claim 1, wherein the composition comprises less than 50% by weight of the benefit agent having mean particle sizes of less than 3 microns.

6. A composition according to claim 1, wherein the composition comprises less than 10% by weight of the benefit agent having mean particle sizes of greater than 80 microns.

7. A composition according to claim 1, wherein the benefit agent in the composition remains as agglomerated particles or droplets when the composition is diluted with distilled water by a factor of 10.

8. A composition according to claim 1, wherein the benefit agent is present in the composition at a level of 4–25% by weight.

9. A composition according to claim 1, wherein the surfactant is an anionic surfactant, and is a fatty acyl isethionate or an alkyl ether sulphate.

10. A composition according to claim 1, wherein the cationic polymer is present at levels of 0.5–1.5% by weight of the composition.

11. A composition according to claim 1, additionally comprising an auxiliary structurant.

12. A composition according to claim 1, additionally comprising a co-surfactant.

13. A composition according to claim 1, additionally comprising a vicosity modifier.

14. A composition according to claim 13 wherein the viscosity modifier is a polypropylene glycol.

15. A composition according to claim 1 wherein the cationic polymer is at least partially hydrated.

16. A composition according to claim 15 wherein the cationic polymer is fully dispersed in the aqueous solution prior to it being fully hydrated.

17. A method of making a compositon according to claim 1, wherein the cationic polymer is predispered in a non-aqueous liquid, which is then dispersed in the aqueous liquid composition.

18. A method of making a composition according to claim 1, wherein the cationic polymer is predispersed in an aqueous solution which has a pH of at least 10, which is then dispersed in the aqueous composition.

* * * * *